United States Patent [19]

Deluca et al.

[11] Patent Number: 5,395,830
[45] Date of Patent: Mar. 7, 1995

[54] METHOD OF TREATING OSTEOPOROSIS WITH 1α,24(R)-DIHYDROXY-22(E)-DEHYDRO-VITAMIN D$_3$

[75] Inventors: Hector F. Deluca, Deerfield; Heinrich K. Schnoes, Madison, both of Wis.

[73] Assignee: Wisconsin Alumni Research Foundation, Madison, Wis.

[21] Appl. No.: 180,105

[22] Filed: Jan. 12, 1994

Related U.S. Application Data

[63] Continuation of Ser. No. 873,374, Apr. 24, 1992, abandoned.

[51] Int. Cl.$^6$ .............................................. A61K 31/59
[52] U.S. Cl. ..................................... 514/167; 514/168; 552/653
[58] Field of Search .................. 514/167, 168; 552/653

[56] References Cited

U.S. PATENT DOCUMENTS

| | | | |
|---|---|---|---|
| 3,833,622 | 9/1974 | Babcock et al. | 552/653 |
| 3,901,928 | 8/1975 | Hesse et al. | 552/653 |
| 4,255,596 | 3/1981 | Wu et al. | 568/860 |
| 4,260,549 | 4/1981 | DeLuca et al. | 552/653 |
| 4,267,117 | 5/1981 | Salmond | 552/653 |
| 4,588,528 | 5/1986 | DeLuca et al. | 514/167 |
| 4,588,716 | 5/1986 | DeLuca et al. | 514/167 |
| 4,590,184 | 5/1986 | Maeda et al. | 514/167 |
| 4,719,204 | 1/1988 | DeLuca et al. | 514/167 |
| 4,822,609 | 4/1989 | Flora | 424/112 |
| 4,833,125 | 5/1989 | Neer et al. | 514/12 |
| 4,997,824 | 3/1991 | Popovtzer et al. | 514/167 |
| 5,001,118 | 3/1991 | Maeda et al. | 552/653 |
| 5,053,401 | 10/1991 | Matsumoto et al. | 514/167 |
| 5,104,864 | 4/1992 | DeLuca et al. | 514/167 |

OTHER PUBLICATIONS

Chem. Pharm. Bull., No. 32, 1984, pp. 3866–3872, Hiroshi Sai et al, 'Synthesis and Biological Activity of (22E,24R) and (22E,24S)–1α,24–dihydroxy–22–dehydrovitamin D$_3$'.

Calcif. Tissue Int., vol. 49, No. Supp, 1991, pp. S46–S49, Christel Lamberg-Allartdt "Is there a role for vitamin D in osteoporosis".

Clinical Endocrinology, No. 16, 1982, pp. 515–524, G. Finn Jensen et al, "Treatment of Post Menopausal Osteoporosis".

Primary Examiner—Raymond J. Henley, III
Assistant Examiner—T. J. Criares
Attorney, Agent, or Firm—Andrus, Sceales, Starke & Sawall

[57] ABSTRACT

A method of treating osteoporosis comprising the administration of an effective amount of 1α,24(R)-dihydroxy-22(E)-dehydro-vitamin D$_3$.

9 Claims, No Drawings

METHOD OF TREATING OSTEOPOROSIS WITH 1α,24(R)-DIHYDROXY-22(E)-DEHYDRO-VITAMIN $D_3$

This invention was made with United States Government support awarded by the National Institute of Health (NIH), Grant No. DK 14881. The United States Government has certain rights in this invention.

This application is a continuation of application Ser. No. 07/873,374, filed Apr. 24, 1992, now abandoned.

BACKGROUND OF THE INVENTION

This invention relates to a method for treating or for preventing the depletion of calcium from bones as a result of osteoporosis.

More specifically, this invention relates to a method for treating or preventing various known forms of osteoporosis, e.g. postmenopausal, senile and steroid-induced osteoporosis, one of the characteristics of which is the loss of bone mass.

It is well known that females at the time of menopause suffer a marked loss of bone mass giving rise ultimately to osteopenia, which in turn gives rise to spontaneous crush fractures of the vertebrae and fractures of the long bones. This disease is generally known as postmenopausal osteoporosis and presents a major medical problem, both in the United States and most other countries where the life-span of females reaches ages of at least 60 and 70 years. Generally, the disease which is often accompanied by bone pain and decreased physical activity, is diagnosed by one or two vertebral crush fractures with evidence of diminished bone mass. It is known that this disease is accompanied by diminished ability to absorb calcium, decreased levels of sex hormones, especially estrogen and androgen, and a negative calcium balance.

Similar symptoms of bone loss characterize senile osteoporosis and steroid-induced osteoporosis, the latter being a recognized result of long term glucocorticoid (cortico-steroid) therapy for certain disease states.

Methods for treating the disease have varied considerably but to date no totally satisfactory treatment is yet known. A conventional treatment is to administer a calcium supplement to the patient. However, calcium supplementation by itself has not been successful in preventing or curing the disease. Another conventional treatment is the injection of sex hormones, especially estrogen, which has been reported to be effective in preventing the rapid loss of bone mass experienced in postmenopausal women. This technique, however, has been complicated by the fear of its possible carcinogenicity. Other treatments for which variable results have been reported, have included a combination of vitamin D in large doses, calcium and fluoride. The primary problem with this approach is that fluoride induces structurally unsound bone, called woven bone, and in addition, produces a number of side effects such as increased incidence of fractures and gastrointestinal reaction to the large mounts of fluoride administered. Another suggested method is to block bone resorption by injecting calcitonin or providing phosphonates.

U.S. Pat. No. 4,225,596 suggests the use of various metabolites of vitamin $D_3$ for increasing calcium absorption and retention within the body of mammals displaying evidence of or having a physiological tendency toward loss of bone mass. The metabolites specifically named in that patent, i.e., 1α-hydroxyvitamin $D_3$, 1α-hydroxyvitamin $D_2$, 1α,25-dihydroxyvitamin $D_3$, 1α,25-dihydroxyvitamin $D_2$ and 1,24,25-trihydroxyvitamin $D_3$, although capable of the activity described and claimed in that patent, are also characterized by the disadvantage of causing hypercalcemia, especially if used with the conventional calcium supplement treatment. Therefore, use of these compounds to treat osteoporosis has not been widely accepted. U.S. Pat. Nos. 3,833,622 and 3,901,928 respectively suggest using the hydrate of 25-hydroxyvitamin $D_3$ and 1α-hydroxyvitamin $D_3$ for treatment of osteoporosis in a general expression of utility for those compounds. It is well known that both of those compounds express traditional vitamin D-like activity, including the danger of hypercalcemia.

U.S. Pat. No. 4,588,716 also suggests the use of 1α,25-dihydroxy-24-epi-vitamin $D_2$ to treat bone disorders characterized by the loss of bone mass, such as osteoporosis. Although this compound expresses some of the vitamin D-like characteristics affecting calcium metabolism such as increasing intestinal calcium transport and stimulating the mineralization of new bone, it has the advantage of minimal effectiveness in mobilizing calcium from bone. The 24-epi compound may be administered alone or in combination with a bone mobilization-inducing compound such as a hormone or vitamin D compound such as 1α-hydroxyvitamin $D_3$ or $D_2$, or 1α,25-dihydroxyvitamin $D_3$ or $D_2$.

SUMMARY OF THE INVENTION

It has now been found that the loss of bone mass, which is characteristic of osteoporosis may be effectively treated by the administration of a 1α-hydroxylated vitamin $D_3$ compound in sufficient amounts to increase bone mass. More specifically, a method of treating osteoporosis comprises the administration of an effective amount of 1α,24(R)-dihydroxy-22(E)-dehydro-vitamin $D_3$. The above compound may be administered alone or in combination with other pharmaceutically acceptable agents. Dosages of from not less than about 0.5 μg/day to not more than about 8 μg/day of the individual compound per se, or in combinations, are generally effective. This method has the distinct advantage that it will restore bone mass due to the insignificant bone mobilization activity of this compound and further this compound advantageously will not cause hypercalcemia even if the compound is administered continuously on a daily basis, as long as the appropriate compound dosages are used, it being understood that the dosage levels will be adjusted dependent on the response of the subject as monitored by methods known to those skilled in the art.

The above method, involving the administration of the indicated dosages of 1α,24(R)-dihydroxy-22(E)-dehydro-vitamin $D_3$ compound is effective in restoring or maintaining bone mass, and thus provides a novel method for the treatment or prevention of various forms of osteoporosis such as postmenopausal osteoporosis, senile osteoporosis and steroid-induced osteoporosis. It will be evident that the method will find ready application for the prevention or treatment of disease states other than those named, in which the loss of bone mass is an indication.

DISCLOSURE OF THE INVENTION

The vitamin D compound useful in the present treatment is 1α,24(R)-dihydroxy-22(E)-dehydro-vitamin $D_3$. The above compound may be administered alone or in combination with other pharmaceutically acceptable agents. 1α,24(R)-dihydroxy-22(E)-dehydro-vitamin D₃ is characterized by the following structural formula

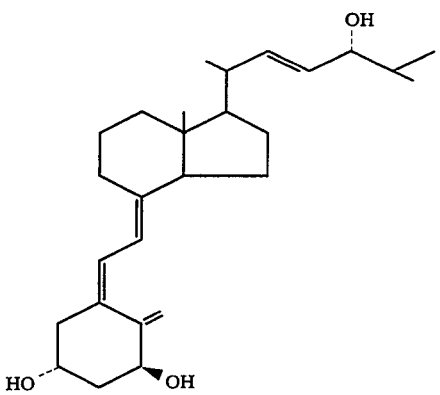

The vitamin D compound or combinations thereof can be readily administered as sterile parenteral solutions by injection or intravenously, or by alimentary canal in the form of oral dosages, or trans-dermally, or by suppository. Doses of from about 0.5 micrograms to about 8 micrograms per day of 1α,24(R)-dihydroxy-22(E)-dehydro-vitamin D₃ compound per se, or in combination with other 1α-hydroxylated vitamin D compounds, the proportions of each of the compounds in the combination being dependent upon the particular disease state being addressed and the degree of bone mineralization and/or bone mobilization desired, are generally effective to practice the present invention. In all cases sufficient amounts of the compound should be used to restore bone mass. Amounts in excess of about 8 micrograms per day of 1α,24(R)-dihydroxy-22(E)-dehydro-vitamin D₃ compound, or the combination of that compound with other 1α-hydroxylated vitamin D compounds, are generally unnecessary to achieve the desired results, may result in hypercalcemia, and may not be am economically sound practice. In practice the higher doses are used where therapeutic treatment of a disease state is the desired end while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art. For example, to be effective, 1α,24(R)-dihydroxy-22(E)-dehydro-vitamin D₃ is preferably administered in a dosage range of 0.5–8 μg/day. In general, either a single daily dose or divided daily dosages may be employed, as is well known in the art.

Dosage forms of the various compounds can be prepared by combining them with non-toxic pharmaceutically acceptable carriers to make either immediate release or slow release formulations, as is well known in the art. Such carriers may be either solid or liquid such as, for example, corn starch, lactose, sucrose, peanut oil, olive oil, sesame oil and propylene glycol. If a solid carrier is used the dosage form of the compounds may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

The following Examples will serve to illustrate the efficacy of the present treatment method and its suitability for the prevention or treatment of osteoporosis.

EXAMPLE 1

This example illustrates that administration of 1α,24(R)-dihydroxy-22(E)-dehydro-vitamin D₃ at the recommended dosages will not mobilize calcium from bone whereas 1α,25(OH)₂D₃ is strongly active in this regard. In animals on a low calcium diet, the elevation of serum calcium reflects the mobilization of calcium from bone.

In the case of the serum calcium data presented in Table I, weanling rats were fed a 0.02% calcium, 0.3% phosphorus vitamin D-deficient diet for three weeks. They were then implanted with Alzet minipumps that delivered the indicated dose of compounds in 95% propylene glycol, 5% ethanol each day for seven days. The rats were then killed and used for everted sac measurement of intestinal calcium transport and serum calcium measurements. The results are illustrated in Table I. The results show that 1α,24(R)-dihydroxy-22(E)-dehydro-vitamin D₃ is almost as active as 1α,25(OH)₂D₃ in causing absorption of calcium from the small intestine, but it shows no activity in mobilizing calcium from bone. In contrast 1α,25(OH)₂D₃ is clearly very active i.e. it raises serum calcium at the expense of bone.

TABLE I

INTESTINAL CALCIUM TRANSPORT AND MOBILIZATION OF CALCIUM FROM BONE IN RESPONSE TO THE VITAMIN D COMPOUNDS

| COMPOUND | DOSE | INTESTINAL CALCIUM TRANSPORT SEROSAL CALCIUM/ MUCOSAL CALCIUM) | SERUM CALCIUM mg % |
|---|---|---|---|
| None | 0 | 3.0 ± 0.2 | 4.2 ± 0.2 |
| 1α,25-(OH)₂D₃ | 130 | 8.5 ± 0.9 | 5.7 ± 0.1 |
| Δ²²,22E-1α,24-(OH)₂D₃ | 130 | 6.0 ± 0.9 | 4.1 ± 0.1 |

EXAMPLE 2

This example illustrates the anti-rachitic activity of 1α,24(R)dihydroxy-22(E)-dehydro-vitamin D₃ in male rats. In this example, weanling male rats were fed a 1.2% calcium, 0.1% phosphorus, vitamin D-deficient diet for three weeks. The indicated dosages of test compounds or 1α,25-(OH)₂D₂ were injected intraperitoneally in 0.1 ml 5% ethanol/95% propylene glycol daily for 7 days. The rats were killed and their femurs removed for bone ash determinations. There were eight rats per group and the values represent the average±S.E.M. The results are illustrated in Table II. The results show that animals treated with 1α,24(R)-dihydroxy-22(E)-dehydro-vitamin D₃ effectively increased bone mass over a control group, and that 1α,24(R)-dihydroxy-22(E)-dehydro-vitamin D₃ is similar in its ability to stimulate new bone formation to 1α,25(OH)₂D₃. This experiment coupled with Example 1 illustrates the extraordinary ability of this compound to elevate bone mass.

TABLE II

ANTI-RACHITIC ACTIVITY OF $\Delta^{22,22E,1\alpha,24}$-DIHYDROXYVITAMIN $D_3$

| GROUP | AMT OF COMPOUND (pmol/day/7 days) | TOTAL Mg Ash | % Ash |
|---|---|---|---|
| -D | 0 | 41 ± 3 | 24.2 ± 2 |
| $1\alpha,25$-$(OH)_2D_3$ | 65 | 55 ± 2 | 27 ± 1 |
|  | 195 | 57 ± 8 | 29 ± 2 |
| $\Delta^{22,22E}$-$1\alpha,24$-$(OH)_2D_3$ | 65 | 42 ± 2 | 23 ± 2 |
|  | 195 | 51 ± 5 | 25 ± 3 |

EXAMPLE 3

This example illustrates that the compound of the present invention is effective for restoring bone mass of rats made osteoporatic by ovariectomy. Mature female rats were obtained from the Sprague Dawley Company of Madison, Wis. either as sham-operated or as oophorectomized rats. The animals were placed on a 0.25% calcium, 0.3% phosphorus, purified diet for three weeks at which time 8 sham-operated and 8 oophorectomized rats were sacrificed. At this time, both groups had 400 mg of ash per femur and the percent ash was 61±2%, indicating fully mineralized skeleton or a lack of any evidence of osteomalacia. The rats were then divided into groups of 8 according to the Table below. They were allowed to proceed on the diet for approximately 5 months in order to reduce mineral content of the femur. At this time, the animals were divided into the appropriate groups and dosed for 18 days with the compounds listed. The dosing was carried out in 95% propylene glycol/5% ethanol solution in an Alzet minipump that delivered 13 μL solution per day and provided the indicated dose in pmol. At the end of the 18-day period, the animals were killed, the femurs removed, extracted with ethanol for 24 hours and with chloroform for 24 hours using a Soxhlet extractor and then dried to constant weight. They were then subjected to muffle furnace temperatures of 600° C. for 24 hours. The remaining ash was dried to constant weight and recorded. The values represent total ash per femur or percent ash. There were eight animals per group and the results are expressed as the mean±S.E.M. The results are illustrated in Table III. A comparison between the sham operated and oophorectomized animals reveals the bone lost as a result of estrogen lack. The increase in bone mass above the oophorectomized control in the dosed animals reveals the degree of bone restoration. It is clear from the data in Table III that $\Delta^{22,22E}$-$1\alpha,24$-$(OH)_2$-$D_3$ is more effective than $1\alpha,25$-$(OH)_2$-$D_3$ in restoring bone mass at the 65 pmol/day dosage as shown by the significantly higher mg femur ash i.e. 424±15 mg versus 388±7.1 mg. As a result, $\Delta^{22,22E}$-$1\alpha,24$-$(OH)_2$-$D_3$ is effective for restoring bone mass.

TABLE III

THE RESTORATION OF BONE BY $1\alpha,25$-$(OH)_2D_3$ AND $\Delta^{22,22E}$-$1\alpha,24$-$(OH)_2$-$D_3$ IN OOPHORECTOMIZED ADULT FEMALE RATS

| GROUP | DOSE (pmol/day) | BODY WEIGHT | FEMUR ASH % | FEMUR ASH mg |
|---|---|---|---|---|
| Sham-operated | 0 | 282 ± 6 | 62 ± 0.3 | 411 ± 7.8 |
| Oophorectomized (OOX) | 0 | 354 ± 11 | 59 ± 1.6 | 350 ± 2.4 |
| OOX + $1\alpha,25$-OH-$D_3$ | 65 | 372 ± 7.0 | 59 ± 0.5 | 388 ± 7.1 |
| OOX + $\Delta^{22,22E}$ $1\alpha,24$-$(OH)_2$-$D_3$ | 65 | 366 ± 17 | 60 ± 0.6 | 424 ± 15 |
|  | 195 | 372 ± 7.3 | 60 ± 0.4 | 429 ± 10 |

We claim:

1. A method of treating osteoporosis by stimulating intestinal calcium transport activity without increasing bone calcium mobilization activity comprising administering to a patient an effective amount of $1\alpha,24(R)$-dihydroxy-22(E)-dehydro-vitamin $D_3$, said effective amount comprising from about 0.5 micrograms to about 8 micrograms per day.

2. The method of claim 1 wherein the osteoporosis is postmenopausal osteoporosis.

3. The method of claim 1 wherein the osteoporosis is senile osteoporosis.

4. The method of claim 1 wherein the osteoporosis is steroid-induced osteoporosis.

5. The method of claim 2 wherein the vitamin $D_3$ compound is administered to women during and subsequent to menopause.

6. The method of claim 1 wherein the vitamin $D_3$ compound is administered to a woman in need thereof prior to the onset of menopause.

7. The method of claim 1 wherein the vitamin $D_3$ compound, in solution in a liquid vehicle ingestible by and nontoxic to said patient, is administered orally in encapsulated form.

8. The method of claim 1 wherein the vitamin $D_3$ compound is administered in a slow release formulation.

9. The method of claim 1 wherein the vitamin $D_3$ compound is administered daily in divided dosages.

* * * * *